(12) United States Patent
Buelna

(10) Patent No.: US 6,461,346 B1
(45) Date of Patent: *Oct. 8, 2002

(54) SEALING OCCLUSION CATHETER AND METHOD OF USING SAME

(75) Inventor: Terrence J. Buelna, Rancho Santa Margarita, CA (US)

(73) Assignee: Applied Medical Resources Corp., Rancho Santa Margarita, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/352,432

(22) Filed: Dec. 9, 1994

Related U.S. Application Data (63) Continuation of application No. 07/873,705, filed on Apr. 22, 1992, now abandoned, which is a continuation of application No. 07/574,454, filed on Aug. 29, 1990, now abandoned.

(51) Int. Cl.[7] .............................................. A61M 29/00
(52) U.S. Cl. ...................... 604/500; 604/514; 604/517; 604/104; 606/198
(58) Field of Search ................. 604/104, 105, 604/54, 55, 500, 514, 515, 516, 517; 606/198

(56) References Cited

U.S. PATENT DOCUMENTS

| | | | | |
|---|---|---|---|---|
| 1,870,942 A | * | 8/1932 | Beatty | 604/105 X |
| 2,106,635 A | * | 1/1938 | Harder | 604/104 |
| 2,230,226 A | * | 2/1941 | Auzin | 604/104 |
| 2,482,622 A | * | 9/1949 | Kahn | 604/104 |
| 2,616,429 A | * | 11/1952 | Merenlender | 604/104 |
| 3,241,554 A | * | 3/1966 | Coanda | 604/105 |
| 3,385,300 A | * | 5/1968 | Holter | 604/104 X |
| 3,970,090 A | * | 7/1976 | Loiacono | 604/104 |
| 3,996,938 A | | 12/1976 | Clark | |
| 4,335,719 A | * | 6/1982 | Johnston | 604/41 |
| 4,572,186 A | * | 2/1986 | Gould et al. | 604/104 X |
| 4,648,383 A | * | 3/1987 | Angelchik | 606/198 X |
| 4,650,466 A | | 3/1987 | Luther | |
| 4,762,127 A | | 8/1988 | Narayanan | |
| 4,773,393 A | | 9/1988 | Haber | |
| 4,944,732 A | * | 7/1990 | Russo | 604/105 X |
| 4,995,868 A | | 2/1991 | Brazier | |
| 5,002,560 A | * | 3/1991 | Machold et al. | 606/198 |
| 5,041,093 A | * | 8/1991 | Chu | 606/198 X |
| 5,090,959 A | * | 2/1992 | Samson et al. | 606/194 |
| 5,443,449 A | | 8/1995 | Buelna | |

FOREIGN PATENT DOCUMENTS

| | | | |
|---|---|---|---|
| GB | 1205743 | * | 9/1970 |
| WO | WO98/52475 | | 11/1998 |

* cited by examiner

*Primary Examiner*—Michael H. Thaler
(74) *Attorney, Agent, or Firm*—Pillsbury Winthrop LLP (57) ABSTRACT

A medical instrument adapted for disposition a relative to an orifice defined in a body wall or for disposition in a passage in a body is provided. The medical instrument includes an elongate tube portion having a handle disposed at one end thereof, and an expandable section disposed near the other end thereof. The expansion member is expandable to form a seal between the expansion member and a surface of the body wall orifice or the body passage around substantially an entire circumference of the expansion member.

27 Claims, 6 Drawing Sheets

SEALING OCCLUSION CATHETER AND METHOD OF USING SAME

This is a continuation, of application Ser. No. 07/873,705, filed Apr. 22, 1992 now abandoned, which is a continuation of Ser. No. 07/574,454, filed Aug. 29, 1990 now abandoned.

BACKGROUND OF THE INVENTION

1. Field of the Invention

This invention relates generally to catheters adapted for sealing and/or occluding cavities and vessels, tubes or other body conduits.

2. Description of the Prior Art

Patients complaining of lower abdominal pain or hematuria (blood in the urine) are often suspect for blockages in the ureter, a relative long, narrow tube which extends from each of the kidneys to the bladder. These blockages may result from kidney stones, tumors, strictures or other obstructions.

The most noninvasive way for determining whether there is a blockage in the ureter is to perform an IV pyleogram. This procedure calls for the intravenous injection of a contrast media or dye into the arm of the patient. This dye eventually collects in the kidneys and passes into the ureters. By using known X-ray fluoroscopic methods, the path of the d ye can be determined. If there is a blockage in the ureter, the path of the dye stops at this blockage providing a contrast in the X-ray which shows the location of the obstruction. If there is more than one obstruction, the dye will be blocked at the first obstruction and may not flow beyond that point. Additional blockages further down the ureter would not be apparent using this intravenous procedure.

Under these conditions, it is sometimes desirable to perform a retrograde procedure which requires that dye be injected at the lower end of the ureter and forced upwardly from the bladder toward the kidney. Although this procedure is quite effective in providing a fluoroscopic view of the lower regions of the ureter, it is somewhat more invasive than the intravenous procedure in that it calls for introduction of an injection catheter through the urethra, into the bladder, and through the ureter orifice into the ureter.

In order to provide suitable visualization of this region, the injection catheter is typically introduced through the working channel of a cystoscope. After the catheter has been positioned, the dye is introduced at the lower end of the ureter and forced upwardly against the force of gravity toward the kidneys. This can present a problem as the dye tends to flow downwardly into the bladder rather than upwardly toward the kidney. In the past, some injection catheters have been provided with enlarged silicone bulbs at their distal ends. These bulbs have been held against the ureter orifice in order to seal the orifice against the downward flow of the dye.

The sealing bulbs have required a size such as fourteen French (14F), a diameter which is sufficient to extend across the normal width of a ureter orifice. While rigid cystoscopes have provided working channels of approximately 14F, the much preferred flexible cystoscopes have working channels of only 7F or 8F. In order to use the injection catheters with the flexible cystoscopes, the catheters have required frontloading, that is they have been introduced through the distal end of the cystoscope toward the proximal end of the cystoscope. After the dye has been injected it is desirable to remove the injection catheter. However, with the relative large seating bulb it has been impossible to withdraw the catheter through the relatviely small working channel of the cystoscope. As a consequence, in order to remove these injection catheters, it had been necessary to remove the entire cystoscope.

What is required is an injection catheter which can be introduced through the narrow channel of a flexible cystoscope, subsequently expanded to block the ureter orifice, and ultimately contracted to permit removal while the cystoscope is left in place.

Catheters of the past have included balloon as well as mesh structures which are expandable from a low profile state. However, the shape of these devices in their expanded state has tended to be round or spherical in cross-section so they have not provided suitable shapes for occluding an orifice. In the case of the mesh structures, the catheters have been adapted solely for embolectomy procedures wherein the expanded mesh structure is used to push blood clots through the vessels. Typically these catheters have not been suitable for injection purposes because the mesh has been porous.

SUMMARY OF THE INVENTION

These problems associated with the prior art have been overcome with the present invention which provides a catheter having a tube means adapted for insertion through a body orifice to dispense an injectate into a body conduit or cavity on the other side of the orifice. A mesh tube is provided proximally of the injection port at the end of the catheter tube means. In a particular embodiment this mesh is expandable from approximately 5F to 14F and presents a generally conical surface at its distal end. A suitable silicone can be applied to seal the mesh so that the injectate can flow through the mesh to the injection port at the end of the catheter.

With the injection port positioned in the ureter, the catheter can be moved forward to bring the expanded mesh into contact with the ureter orifice. In this location the expanded mesh forms a seal with the walls of the ureter near the bladder. The seal prevents the injected dye from moving downwardly so that it tends to travel upwardly toward the kidneys.

In one aspect of the invention, the mesh tube has a distal end and a proximal end, and means is provided for the relative movement of the distal end toward the proximal end. This causes the intermediate regions of the tube to expand outwardly thereby providing the tube with an increased diameter and a preferred conical shape. Disposition of the silicone on the tubular mesh can facilitate various other shapes for the mesh in its expanded state.

In a preferred method for making the catheter, a section of the mesh tubing is disposed axially on a mandrel and its ends are bonded to inhibit fraying. The distal end of an injection catheter is moved onto the mandrel in abutting relationship with the mesh subassembly. A tubing sleeve can then be glued over the butt joint between the catheter and the tube. With the mandrel still in place, a coating of silicone can be applied over the mesh to seal the expandable structure. The mandrel is ultimately removed to clear the injection channel which extends through the catheter and the mesh tube.

Finally a wire, or other tension means, is introduced down the injection channel and crimped around the distal end of the mesh tube. In operation, this wire is pulled proximally within the catheter to draw the distal end of the mesh tube toward the proximal end of the mesh tube. This provides the desired expansion and shape for sealing/occluding an orifice, tube, or cavity.

These and other advantages associated with the instant invention would be more apparent with a discussion of preferred embodiments of the concept in reference to the associated drawings.

DESCRIPTION OF PREFERRED EMBODIMENTS

Figure 1:
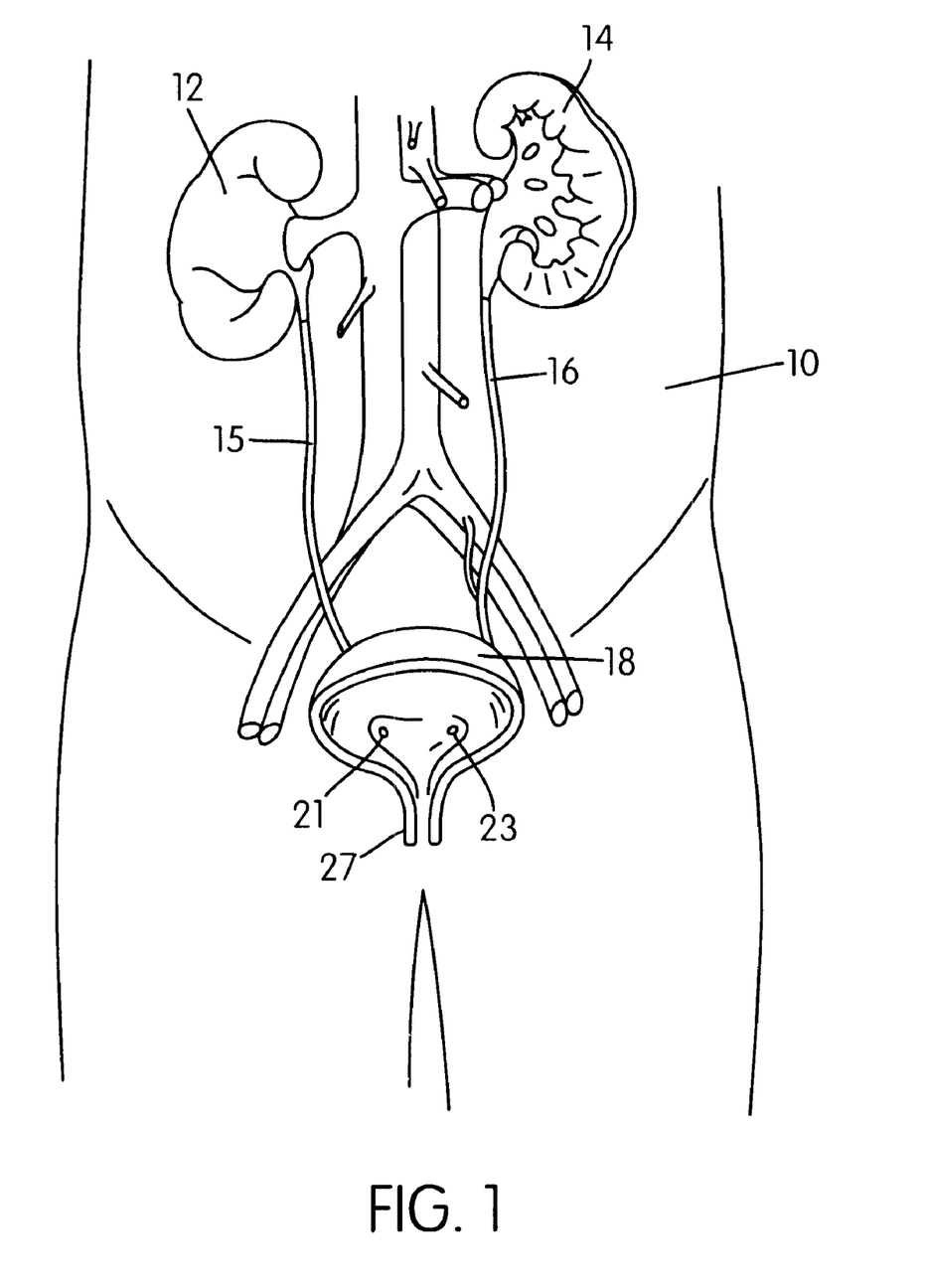
FIG. 1 is a pictorial illustration of the kidneys, the bladder, and the ureters which extend therebetween.

A human body is illustrated in FIG. 1 and designated by the reference numeral 10. A pair of kidneys 12 and 14 are disposed in the lumbar region of the body 10 and function to filter the blood, excreting the end-products of body metabolism in the form of urine. This urine is introduced through a pair of ureters 15 and 16 which are associated with the kidneys 12 and 14, respectively. From the ureters 15, 16 the urine flows into a common bladder 18 through respective ureter orifices 21 and 23. The urine is emptied from the body through a urethra 27.

In the following description, reference will be made primarily to the kidney 14, ureter 16, and orifice 23 on the left side of the body 10. However, the comments may apply equally to the kidney 12, ureter 15, and orifice 21 on the right side of the body 10.

Figure 2:
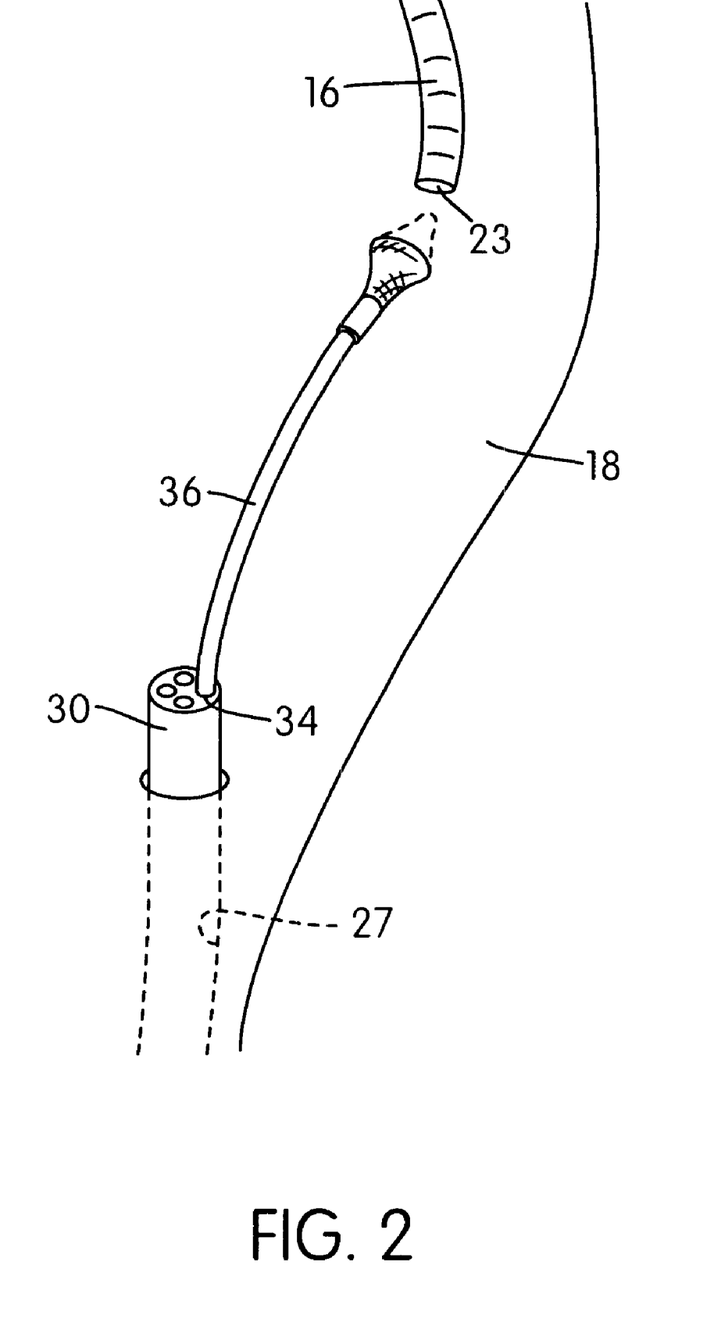
FIG. 2 is an enlarged side elevation view of the cystoscope and an catheter associated with the present invention, operatively disposed in the bladder to perform a retrograde pylogram.

In a procedure involving a retrograde ureter pylogram, a cystoscope 30 is introduced through the urethra 27 and into the bladder 18. The cystoscope 30 provides means for visualizing the interior region of a body conduit or cavity from a location at the proximal end of the cystoscope. Fiberoptics provide light at the distal end of the cystoscope and communicate images back to an eyepiece (not shown) at the proximal end of the cystoscope 30.

Of particular interest in the cystoscope 30 is a working channel 34 which extends through the cystoscope 30. Although this working channel 34 is quite narrow, approximately 7F or 8F, it nevertheless is configured to receive various instruments such as brushes, clips, biopsy devices and stone removal baskets. In accordance with the present procedure, an injection catheter 36 is introduced through the working channel 34 in the cystoscope 30.

Figures 3, 4:
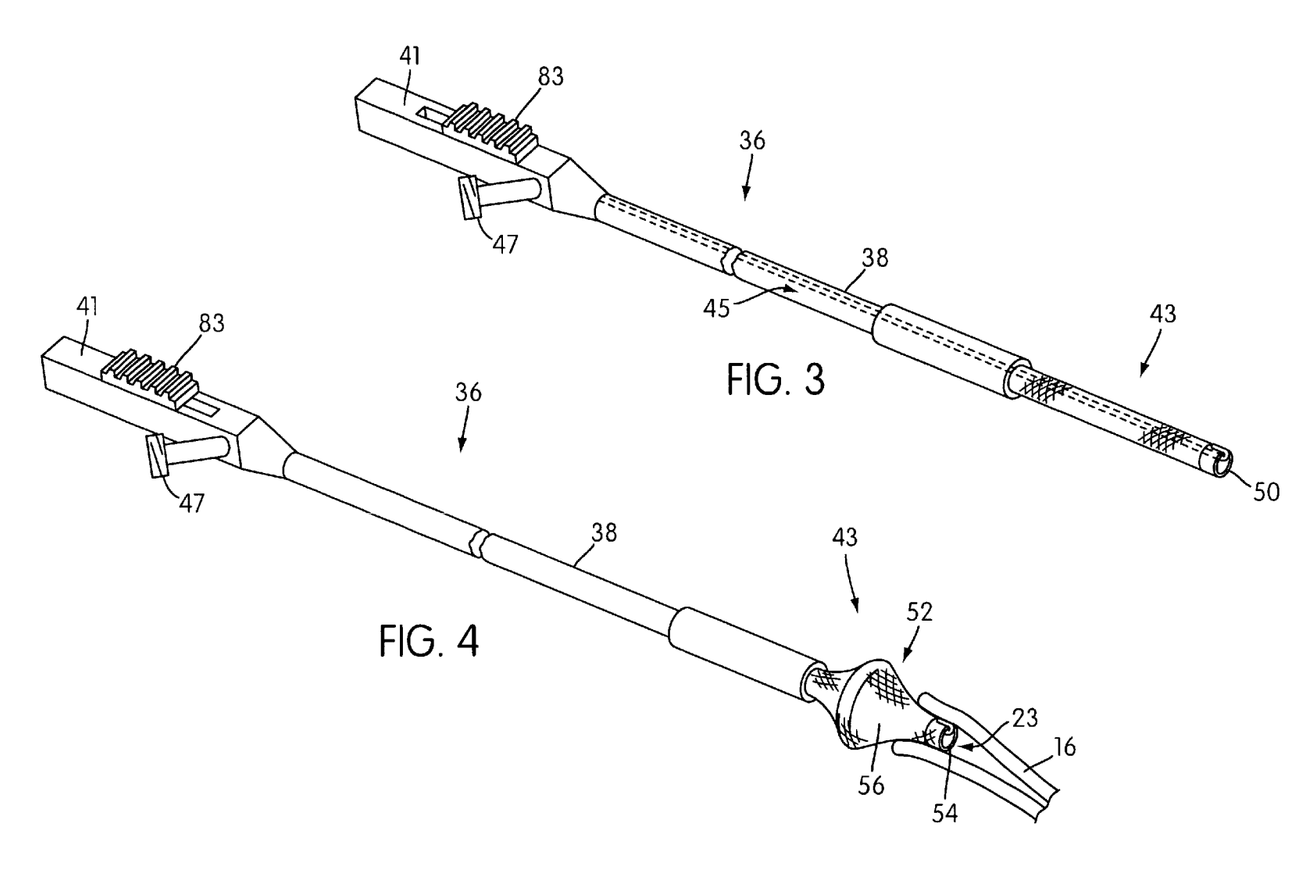
FIG. 3 is a perspective view of the catheter illustrating an expandable mesh section in a contracted state.
FIG. 4 is a perspective view similar to FIG. 3 illustrating the expandable mesh section in an expanded state.

The catheter 36 is perhaps best illustrated in FIGS. 3 and 4. It can include a tube means comprising an elongate flexible tube 38 having a handle 41 disposed at its proximal end, and an expandable section 43 disposed near its distal end. An injection channel 45 extends from a Leur hub 47 at the handle 41, through the tube 38 and the expandable section 43, to exit the catheter 36 at an injection port 50.

In a procedure involving a retrograde polyogram, the flexible tube 38 of the catheter 36 is introduced through the working channel 34 of the cystoscope 30, and the distal port 50 of the catheter is directed through the ureter orifice 23 into the ureter 16. With the injection port 50 thus positioned, the dye can be injected through the Leur hub 47 and the channel 45 to exit the injection port 50 into the ureter 16.

Of particular interest to the present invention is the expandable section 43 of the catheter 36. It is this section 43 which can be brought into sealing engagement with the ureter orifice 23 to inhibit a flow of the injected dye back into the bladder 18. In FIG. 3, this expandable section 43 is illustrated to have a low profile with a diameter which is substantially equivalent to that of the flexible tube 38. This low profile is particularly desirable when the catheter 36 is being introduced through the narrow working channel 34 of the cystoscope 30.

Operation of the catheter 36 expands the diameter of the section 43 as illustrated in FIG. 4. In the case of an embodiment adapted for sealing the ureter orifice 23, it is particularly desirable that the section 43 expand in the shape of cone shown generally at 52 with the apex 54 of the cone 52 facing distally of the catheter 36. This shape provides a generally concave surface 56 which faces the orifice 23. In another aspect of the invention, the surface 56 of the cone 52 progresses radially outwardly with progressive positions from the apex 54 proximally to the base of the cone 52.

Figure 5:
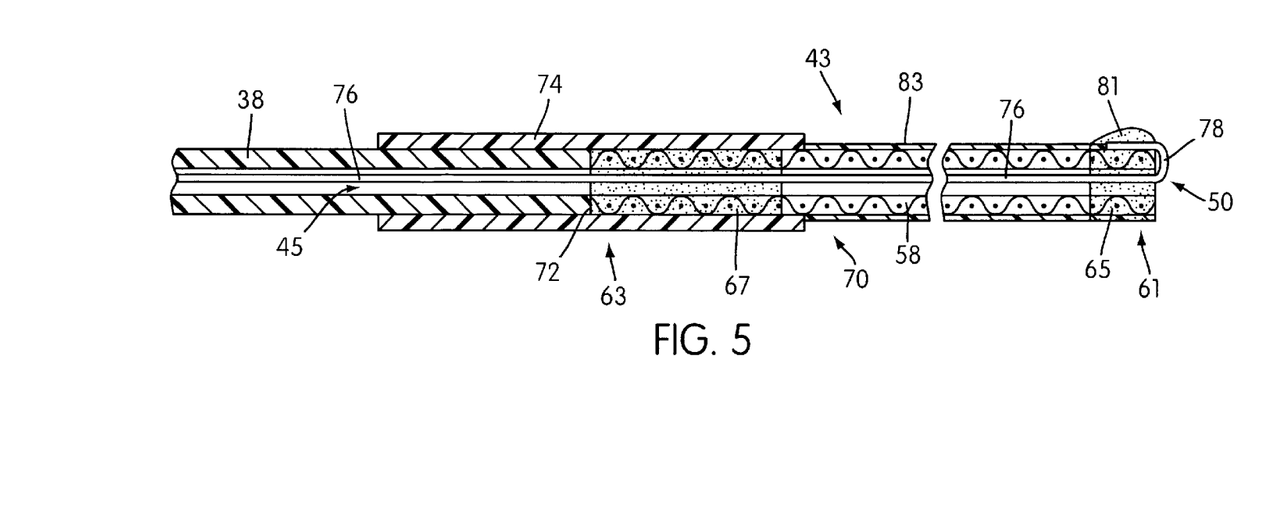
FIG. 5 is a cross-sectional view of the catheter illustrating the expandable mesh section at the distal end of the catheter.

Referring to the embodiment of FIG. 5, the section 43 is illustrated to include an expandable tube 58 having a distal end 61 and a proximal end 63. Each of the ends 61 and 63 are provided with an adhesive coating 65 and 67 respectively. These coatings prevent the mesh tube 58 from fraying or unraveling. In a preferred embodiment the proximal end 63 of the tube 58 and the distal end of the catheter tube 38 form a butt joint 72. This joint 72 can be covered with a sleeve 74 which is attached by a suitable adhesive to the catheter tube 38 and the expandable tube 58.

In the expandable section 43, the tube 58 is representative of any tubular material which has sufficient flexibility and elasticity to permit the ends of the tubes 61, 63 to be moved axially inwardly (toward each other) thereby causing the central regions of the tube 58 to expand radially outwardly. This of course increases the diameter of the tube 58.

These characteristics are particularly apparent when the tube 58 is made from mesh as illustrated in FIG. 5. In this embodiment, means for drawing the distal end 61 toward the proximal end 63 is provided in the form of a wire 76 which extends from the proximal end of the catheter 36, through the channel 45 and the expandable tube 58, to exit the catheter through the injection port 50. Beyond the port 50, the wire 76 can be bent back on itself around the distal end 61 of the expandable tube 58. In a preferred embodiment, this end 78 of the wire 76 is held in place by a suitable adhesive 81.

In other embodiments it may be desirable to attach the wire 76 at a more proximate position. In general, the wire 76 can accomplish its function if its distal end is attached to the catheter 36 at any location which is distal to the end 61 of the expandable tube 58.

The wire 76 is representative of any tension means having properties for extending through a first end of a tube and engaging a second end of the tube to draw the second end toward the first end of the tube. The wire also functions as a compression means having properties for extending through the first end of the tube and engaging the second end of the tube to push the second end away from the first end of the tube.

At the proximal end of the catheter 36, the wire 76 can be attached to a thumb slide 83 which is engagable by the thumb of the user. In a preferred embodiment, the slide 83 is movable on the handle 41 from a proximal position illustrated in FIG. 3 to a distal position illustrated in FIG. 4.

With the wire 76 connected to the distal end 61 of the expandable tube 58, movement of the thumb slide 83 from its distal position to its proximal position will draw the distal end 61 of the expandable tube 58 toward the proximal end 63. Those regions of the tube 58 which are disposed between the ends 61 and 63 are forced to expand outwardly thereby increasing the diameter of the tube 58.

Particularly in those embodiments relying upon the integrity of the channel 45, it is desirable that the expandable tube 58 have solid walls so that the channel 45 extends through the tube 58 to the injection port 50. When the expandable tube 58 is formed from a mesh material, it is desirable to provide the mesh with a coating 83 of a solid material such as silicone.

Figure 9:
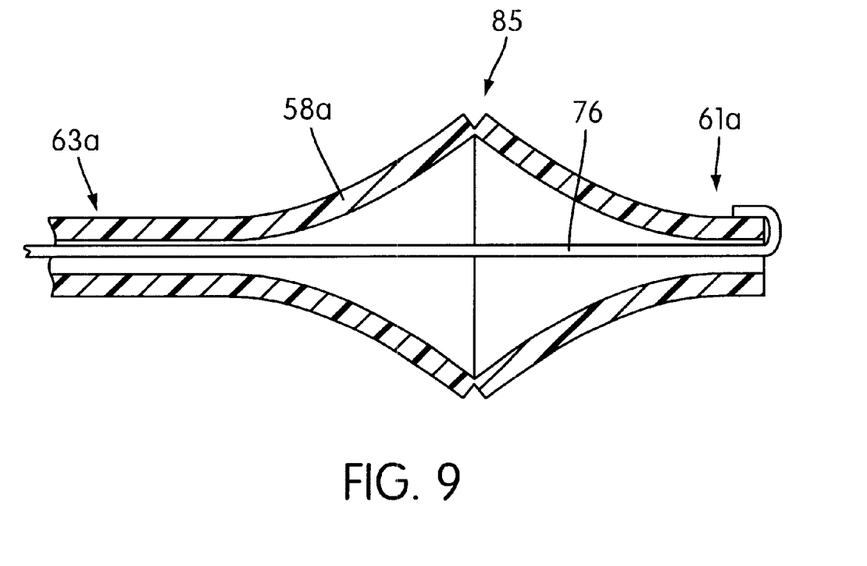
FIG. 9 is a further embodiment of the present invention including an expandable section formed from silicone and including a living hinge.

The expandable tube 58 can be formed from materials other than mesh and can even be configured to provide the tube 58 in its expanded state with shapes other than that of the cone 52. For example, the expandable tube 58 may be formed from a silicone tube 58a having a distal end 61a and a proximal end 63a. As illustrated in FIG. 9, this tube 58a can be provided with an exterior circumferential cut out 85 to form an area of weakness between the ends 61a and 63a. Then when the ends 61a, 63a are brought into proximity, the cut out 85 functions as a living hinge to facilitate the radial expansion and conical shape of the tube 58a.

Figure 6:
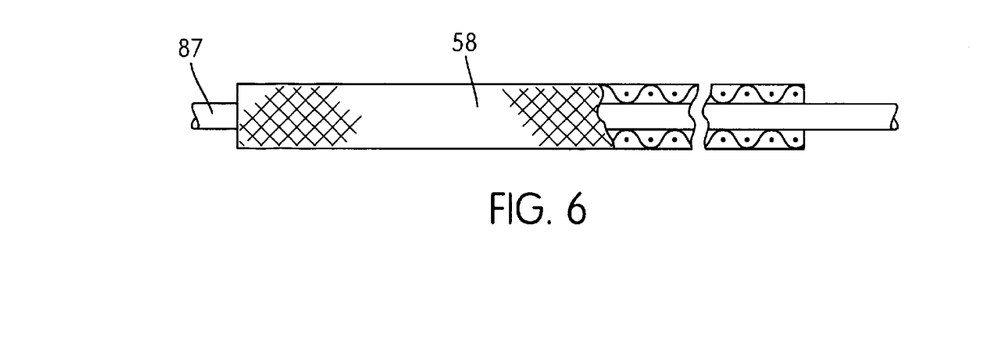
FIG. 6 illustrates a section of mesh disposed on a mandrel in the initial step of a preferred method for manufacturing the catheter.

In a preferred method for manufacturing the catheter 38, the subassembly 70 is initially formed by placing a section of the mesh tubing 58 over a mandrel 87 as illustrated in FIG. 6. In this method the mandrel 87 is coated with Teflon® and provided with a diameter such as 0.020 inches. The mesh tube 58 can be formed from 5 mil. polyester fibers and provided with an inside diameter not less than the diameter of the mandrel 87. The length of the tube 58 is approximately ¾"j in this embodiment.

This combination can be heated in an oven for a period of 15 to 20 minutes at a temperature of 150 degrees F. in order to heat set the polyester mesh.

Figure 7:
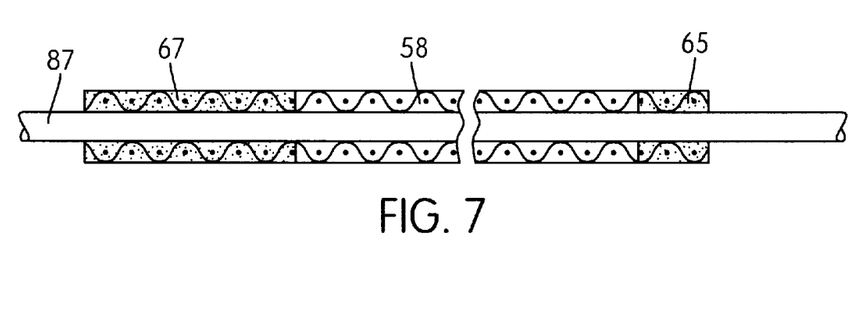
FIG. 7 is a side view of the mesh tube and mandrel of FIG. 6 with adhesive applied to the ends of the mesh tube to form a mesh tube subassembly.

The coatings 65 and 67 can be formed by coating the distal and proximal ends 61, 63 respectively with a suitable UV adhesive such as that manufactured by Loctite and sold under the trademark Improv®. At the distal end 61, the coating 65 preferably has an axial dimension less than 0.060 inches. The coating 67 at the proximal end of the mesh tube 58 does not exceed 0.200 inches. The ends of the mesh tube 58 can then be cut so that the subassembly 70 has a length of about 0.550 inches. The adhesive coatings 65 and 67 can be cured by setting the subassembly 70 under a light source for approximately 40 seconds or until the adhesive has a glazed appearance. The outer diameter of the subassembly 70 does not exceed 0.050 inches in this preferred embodiment.

Figure 8:
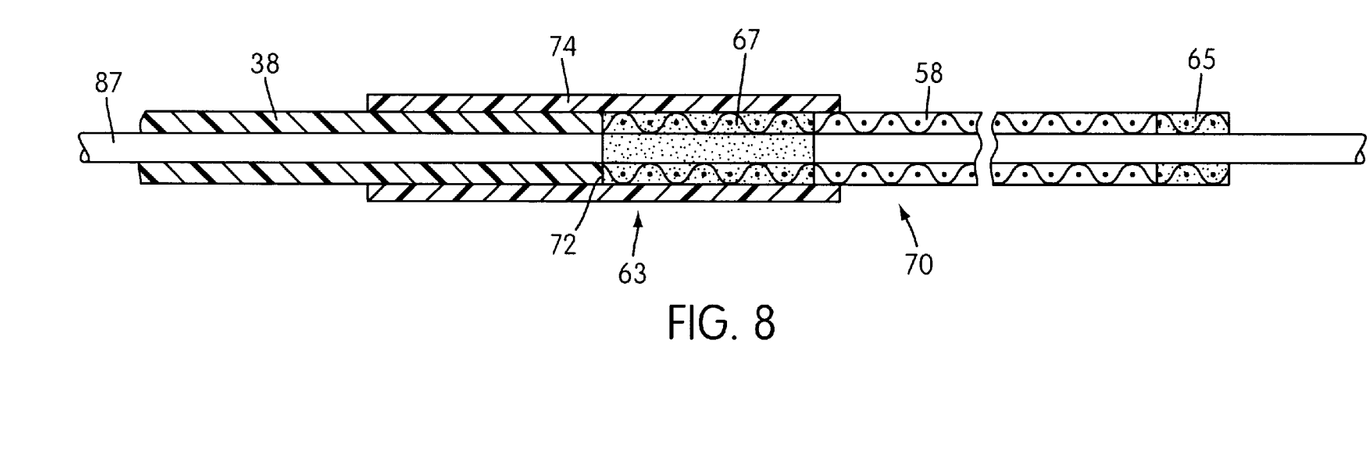
FIG. 8 illustrates a side elevation view of a catheter tube received over the mandrel forming a butt joint with the mesh tube subassembly.

The tube 38 of the catheter 36 can be formed from polyvinylchloride tubing having an outside diameter such as 0.056 inches and cut to a length such as 2 feet. As illustrated in FIG. 8, the tube 38 can be guided onto the mandrel 87 and moved into abutting relationship at the proximal end 63 of the subassembly 70. This forms the butt joint 72 with the mandrel 87 still in place. The sleeve 74 can be provided in the form of a polyamide tubing having an outside diameter such as 0.059 inches and a length such as 0.035 inches. The sleeve 74 can be positioned over the butt joint 72 and bonded with a suitable adhesive, such as cyaroacrylate, to the tube 38 and the subassembly 70.

The silicone coating 83 which fills the interstitices of the mesh tube 58, can be formed by brushing a silicone dispersion such as acetoxy onto the mesh and curing the dispersion in an oven for approximately 30 minutes at a temperature such as 160 degrees F. After this curing step, the catheter 36 can be cooled and the mandrel 87 removed from the channel 45.

At this point, the wire 76 can be introduced into the channel 45 with its distal end extending beyond the injection port 50. This wire in a preferred embodiment had a diameter of 0.009 inches and is formed from stainless steel. The distal end of the wire can be bent over the coating 65 at the distal end of the flexible tube 58 and fixed with the adhesive 81. At the proximal end of the catheter 36, the wire 76 is attached to the thumb slide 83 as previously discussed.

In particular embodiments of the catheter 36, the silicone coating 87, or the silicone tube 58a in the case of the FIG. 9 embodiment, can be scored or otherwise provided with the cut out 85 to facilitate a particularly desirable shape for the expandable tube 58 in its expanded state.

Although the invention has been described with reference to specific embodiments and preferred steps in a method of manufacture, it will be apparent to those skilled in the art that the invention can be otherwise embodied and the catheter can be otherwise constructed. These variations are all deemed to be part of the broad concept so that the scope of the invention should be ascertained only with reference to the following claims.

What is claimed is:

1. A method for sealing an orifice defined through a body wall and into a body region on the other side of the orifice comprising the steps of:

providing an instrument comprising:

an elongate tube portion having a proximal end, a distal end, and a lumen extending therebetween, an expansion member having a distal end and a proximal end and a peripheral wall extending therebetween, the peripheral wall being formed of a material impervious to liquid and sufficiently flexible to permit the distal end and the proximal end of the expansion member to be moved relative to each other between an expanded state of the peripheral wall wherein the distal end and the proximal end are spaced from each other by a first distance, and a contracted state of the peripheral wall wherein the distal end and the proximal end are spaced from each other by a second distance greater than the first distance, said expansion member extending axially from said distal end of said elongate tube, the expansion member in the expanded state including a portion having the general configuration of a cone with an apex at the distal end of said expansion member, a base proximal of said apex, and an inclined outer surface extending between the apex and the base and facing generally distally, and an operating member fixedly coupled to the expansion member adjacent the distal end of said expansion member, so as to be substantially immovable axially relative to said expansion member distal end, and extending proximally therefrom through at least a portion of said lumen, displacement of said operating member and expansion member distal end coupled thereto proximally relative to said elongate tube portion so as to reduce a distance between said distal end of said expansion member and said distal end of said elongate tube portion forcibly displacing said peripheral wall toward the expanded state;

and performing a procedure including:

introducing the distal end of the expansion member into the body orifice; and displacing said operating member and expansion member distal end fixedly coupled thereto relative to said elongate tube portion so as to reduce a distance between said distal end of said expansion member and said distal end of said elongate tube portion and thereby expand said expansion member with said operating member remaining fixedly coupled thereto and engaging said inclined outer surface with said body wall to form a radial seal between the inclined outer surface and the body wall to inhibit fluid from flowing proximally through the orifice;

said operating member being fixedly coupled to said expandable structure throughout said procedure.

2. The method recited in claim 1 wherein said step of providing an instrument comprises providing an expansion member having a distal orifice and the method further comprises the steps of orienting the distal end of the expansion member within the region so that the seal is formed in proximity to the orifice and injecting an injectate through said distal orifice, distally of the seal.

3. The method recited in claim 1 wherein:

the displacing step includes the step of expanding the peripheral wall of the expansion member, and moving the tube axially to bring the expanded peripheral wall into sealing engagement with the body wall.

4. A method as in claim 1, wherein at least said contracted state is a relaxed state of said expansion member.

5. A method as in claim 1, wherein the distal facing surface of the expansion member is engaged with the body wall at the orifice.

6. A method for introducing an injectate into a body region, comprising the steps of:

inserting an endoscope up to a body wall defining an orifice into the body region, the orifice having a first diameter and the endoscope having a working channel with a second diameter, providing a medical instrument comprising:

an elongate tube portion having a proximal end, a distal end, and a lumen extending therebetween, an expansion structure having a distal end and a proximal end and a peripheral wall extending therebetween, the peripheral wall being formed of a material impervious to liquid and sufficiently flexible to permit the distal end and the proximal end of the expansion structure to be moved relative to each other between an expanded state of the peripheral wall wherein the distal end and the proximal end are spaced from each other by a first distance, and a contracted state of the peripheral wall wherein the distal end and the proximal end are spaced from each other by a second distance greater than the first distance, said expansion structure extending axially from said distal end of said elongate tube portion, and an operating member fixedly coupled to the expansion structure adjacent the distal end of said expansion structure, so as to be substantially immovable axially relative to said expansion structure distal end, and extending proximally therefrom through at least a portion of said lumen, so that displacement of said operating member and expansion structure distal end coupled thereto proximally relative to said elongate tube portion so as to reduce a distance between said distal end of said expansion structure and said distal end of said elongate tube portion displaces said peripheral wall toward the expanded state;

and performing a procedure including:

introducing said medical instrument through the working channel of the endoscope, the instrument being operable between an expanded state characterized by said expansion structure expanded to a third diameter larger than the first diameter of the orifice and larger than the second diameter of the working channel, and a contracted state characterized by said expansion structure contracted to a fourth diameter smaller than the second diameter of the working channel, the outer surface of the expandable structure in its expanded state being non-cylindrical along substantially its entire length and including a portion having a generally conical shape having an apex adjacent the distal end thereof and a base proximal of said apex, and an inclined outer surface extending between the apex and the base and facing generally distally, with the third diameter being defined at a point of maximum expansion along the length of the outer surface;

operating the expandable structure to the non-cylindrical expanded state;

moving the inclined outer surface of the expandable structure in the expanded state into contact with the body wall to form a seal with the body wall;

injecting the injectate through the tube and into the body conduit or cavity while the seal inhibits flow of the injectate through the orifice;

operating the expandable structure to the contracted state; and withdrawing the tube through the working channel of the endoscope;

said operating member being fixedly coupled to said expandable structure throughout said procedure.

7. A method as in claim 6, wherein at least said contracted state is a relaxed state of said expansion member.

8. A method as in claim 6, wherein the distal facing surface of the expansion member is engaged with the body wall at the orifice.

9. A medical instrument adapted for disposition relative to an orifice defined in a body wall, comprising:

an elongate tube portion having a proximal end, a distal end, and a lumen extending therebetween;

an expansion member having a distal end and a proximal end and a peripheral wall extending therebetween, the peripheral wall being formed of a material impervious to liquid and sufficiently flexible to permit the distal end and the proximal end of the expansion member to be moved relative to each other between an expanded state of the peripheral wall wherein the distal end and the proximal end are spaced from each other by a first distance, and a contracted state of the peripheral wall wherein the distal end and the proximal end are spaced from each other by a second distance greater than the first distance and vice versa, said expansion member extending axially from said distal end of said elongate tube, the peripheral wall comprising a circumferential living hinge having a wall thickness less than adjacent portions of the peripheral wall, said living hinge thereby facilitating expansion of said peripheral wall;

the expansion member in the expanded state including a portion having the general configuration of a cone with an apex at the proximal end of said expansion member, a base proximal of said apex, and an inclined outer surface extending between the apex and the base and facing generally outwardly;

an operating member fixedly coupled to the expansion member adjacent the distal end of said expansion member and extending proximally therefrom through at least a portion of said lumen, said operating member being substantially permanently attached to said expansion member distal end whereby said operating member and said expansion member remain coupled throughout an entire procedure in which the medical instrument is used, displacement of said operating member and expansion member distal end coupled thereto relative to said elongate tube portion so as to reduce a distance between said distal end of said expansion member and said distal end of said elongate tube portion forcibly displacing said peripheral wall toward the expanded state, wherein contact of the inclined outer surface of the expansion member in the expanded state with the body wall to exert a pressure on the body wall forms a seal between the expansion member and the body wall, and wherein said inclined outer surface comprises a concave surface extending radially outwardly from the apex to a maximum radius at the base of the cone;

whereby fluid is inhibited from flowing through the orifice.

10. The instrument recited in claim 9, wherein:
the inclined outer surface of the cone extends radially outwardly with progressive positions from the apex of the cone to the base of the cone.

11. The instrument recited in claim 9, wherein the seal is formed in proximity to the base of the cone.

12. The instrument recited in claim 9, wherein said expansion member is integral with said elongate tube portion and extends substantially continuously therefrom.

13. The medical instrument of claim 9, wherein at least said contracted state is a relaxed state of said expansion member.

14. A medical instrument adapted for disposition relative to an orifice defined in a body wall, comprising:
an elongate tube portion having a proximal end, a distal end, and a lumen extending therebetween;
an expansion member having a distal end and a proximal end and a peripheral wall extending therebetween, the peripheral wall being formed of a material impervious to liquid and sufficiently flexible to permit the distal end and the proximal end of the expansion member to be moved relative to each other between an expanded state of the peripheral wall wherein the distal end and the proximal end are spaced from each other by a first distance, and a contracted state of the peripheral wall wherein the distal end and the proximal end are spaced from each other by a second distance greater than the first distance and vice versa, said expansion member extending axially from said distal end of said elongate tube, the peripheral wall comprising a circumferential living hinge having a wall thickness less than adjacent portions of the peripheral wall, said living hinge thereby facilitating expansion of said peripheral wall;

the expansion member in the expanded state including a portion having the general configuration of a cone with an apex at the proximal end of said expansion member, a base distal of said apex, and an inclined outer surface extending between the apex and the base and facing generally proximally;

an operating member fixedly coupled to the expansion member adjacent the distal end of said expansion member and extending proximally therefrom through at least a portion of said lumen, said operating member being substantially permanently attached to said expansion member distal end whereby said operating member and said expansion member remain coupled throughout an entire procedure in which the medical instrument is used, displacement of said operating member and expansion member distal end coupled thereto relative to said elongate tube portion so as to reduce a distance between said distal end of said expansion member and said distal end of said elongate tube portion forcibly displacing said peripheral wall toward the expanded state, wherein contact of the inclined outer surface of the expansion member in the expanded state with the body wall to exert a pressure on the body wall forms a seal between the expansion member and the body wall, and wherein said inclined outer surface comprises a concave surface extending radially outwardly from the apex to a maximum radius at the base of the cone;

whereby fluid is inhibited from flowing through the orifice.

15. The instrument recited in claim 14, wherein:
the inclined outer surface of the cone extends radially outwardly with progressive positions from the apex of the cone to the base of the cone.

16. The instrument recited in claim 14, wherein the seal is formed in proximity to the base of the cone.

17. The instrument recited in claim 14, wherein said expansion member is integral with said elongate tube portion and extends substantially continuously therefrom.

18. The medical instrument of claim 14, wherein at least said contracted state is a relaxed state of said expansion member.

19. A medical instrument adapted for disposition relative to an orifice defined in a body wall, comprising:
an elongate tube portion having a proximal end, a distal end, and a lumen extending therebetween;
an expansion member having a distal end and a proximal end and a peripheral wall extending therebetween, the peripheral wall comprising a woven mesh material, the peripheral wall also being impervious to liquid and sufficiently flexible to permit the distal end and the proximal end of the expansion member to be moved relative to each other between an expanded state of the peripheral wall wherein the distal end and the proximal end are spaced from each other by a first distance, and a contracted state of the peripheral wall wherein the distal end and the proximal end are spaced from each other by a second distance greater than the first distance and vice versa, said expansion member extending axially from said distal end of said elongate tube;
a portion of the expansion member, including a portion of the woven mesh material, when in the expanded state, having the general configuration of a cone with an apex at the distal end of said expansion member, a base proximal of said apex, and an inclined outer surface extending between the apex and the base and facing generally distally;

an operating member fixedly coupled to the expansion member adjacent the distal end of said expansion member and extending proximally therefrom through at least a portion of said lumen, said operating member being substantially permanently attached to said expansion member distal end whereby said operating member and said expansion member remain coupled throughout an entire procedure in which the medical instrument is used, displacement of said operating member and expansion member distal end coupled thereto relative to said elongate tube portion so as to reduce a distance between said distal end of said expansion member and said distal end of said elongate tube portion forcibly displacing said peripheral wall toward the expanded state, wherein contact of the outer surface of the expansion member in the expanded state with the body wall to exert a pressure on the body wall forms a seal between the expansion member and the body wall around substantially an entire circumference of the expansion member, wherein said inclined outer surface comprises a concave surface extending radially outwardly from the apex to a maximum radius at the base of the cone;

whereby fluid is inhibited from flowing through the orifice.

20. The instrument recited in claim 19, wherein:

the inclined outer surface of the cone extends radially outwardly with progressive positions from the apex of the cone to the base of the cone.

21. The instrument recited in claim 19, wherein said expansion member is integral with said elongate tube portion and extends substantially continuously therefrom.

22. The medical instrument of claim 19, wherein at least said contracted state is a relaxed state of said expansion member.

23. A medical instrument adapted for disposition in a passage in a body, comprising:

an elongate tube portion having a proximal end, a distal end, and a lumen extending therebetween;

an expansion member having a distal end and a proximal end and a peripheral wall extending therebetween, the peripheral wall comprising a woven mesh material, the peripheral wall also being impervious to liquid and sufficiently flexible to permit the distal end and the proximal end of the expansion member to be moved relative to each other between an expanded state of the peripheral wall wherein the distal end and the proximal end are spaced from each other by a first distance, and a contracted state of the peripheral wall wherein the distal end and the proximal end are spaced from each other by a second distance greater than the first distance and vice versa, said expansion member extending axially from said distal end of said elongate tube;

a portion of the expansion member, including a portion of the woven mesh material, when in the expanded state, having the general configuration of a cone including an apex, a base and an inclined outer surface extending between the apex and the base;

an operating member fixedly coupled to the expansion member adjacent the distal end of said expansion member and extending proximally therefrom through at least a portion of said lumen, said operating member being substantially permanently attached to said expansion member distal end whereby said operating member and said expansion member remain coupled throughout an entire procedure in which the medical instrument is used, displacement of said operating member and expansion member distal end coupled thereto relative to said elongate tube portion so to reduce a distance between said distal end of said expansion member and said distal end of said elongate tube portion forcibly displacing said peripheral wall toward the expanded state, wherein contact of the outer surface of the expansion member in the expanded state with a surface of the passage to exert a pressure on the surface of the passage forms a seal between the expansion member and the surface of the passage around substantially an entire circumference of the expansion member, and wherein said inclined outer surface comprises a concave surface extending radially outwardly from the apex to a maximum radius at the base of the cone;

whereby fluid is inhibited flowing through the passage.

24. The instrument recited in claim 23, wherein:

the inclined outer surface of the cone extends radially outwardly with progressive positions from the apex of the cone to the base of the cone.

25. The instrument recited in claim 23, wherein said expansion member is integral with said elongate tube portion and extends substantially continuously therefrom.

26. The medical instrument of claim 23, wherein at least said contracted state is a relaxed state of said expansion member.

27. The instrument recited in claim 23, wherein:

the expansion member in the expanded state includes a second portion having the general configuration of a cone including an apex, a base, and an inclined outer surface extending between the apex and the base, the two bases of the cone-configured portions of the expansion member being positioned adjacent each other in a central portion of the expansion member, one of the apexes being positioned proximal the proximal end of the expansion member and the other of the apexes being positioned proximal the distal end of the expansion member.

* * * * *